United States Patent [19]

Travers et al.

[11] Patent Number: 4,943,546

[45] Date of Patent: Jul. 24, 1990

[54] NORMAL PARAFFIN ISOMERIZATION CATALYST COMPRISING A MORDENITE AND TITANIUM

[75] Inventors: Christine Travers, Rueil-Malmaison; Jean-Pierre Franck, Bougival, both of France

[73] Assignee: Institut Français du Petrole, Rueil-Malmaison, France

[21] Appl. No.: 266,594

[22] Filed: Nov. 3, 1988

[30] Foreign Application Priority Data

Nov. 3, 1987 [FR] France .................... 87 15333

[51] Int. Cl.$^5$ .................................. B01J 29/20
[52] U.S. Cl. ............................ 502/66; 502/74; 502/78
[58] Field of Search .......................... 502/66, 78, 74

[56] References Cited

U.S. PATENT DOCUMENTS 3,583,903  6/1971  Maile et al. ..................... 502/78
4,663,300  5/1987  Lester et al. ..................... 502/78

FOREIGN PATENT DOCUMENTS 49803    4/1982  European Pat. Off. .
115188   8/1984  European Pat. Off. ........... 502/74
196965  10/1986  European Pat. Off. ........... 502/78
198720  10/1986  European Pat. Off. .
253743   1/1988  European Pat. Off. .
2593084  7/1987  France .

Primary Examiner—Carl F. Dees
Attorney, Agent, or Firm—Millen, White & Zelano

[57] ABSTRACT

A catalyst comprising by weight:

(a) 10–99.98% of a mordenite, in major part as needles, having a Si/Al atomic ratio of from 5:1 to 100:1, a sodium content lower than 0.2% by weight of the dry mordenite weight, a mesh volume V of elementary mesh from 2.73 to 2.78 nm$^3$, which adsorbs molecules of a kinetic diameter higher than about 6.6 Angströms and has a benzene adsorption capacity higher than about 5% by weight, (b) 0–89.98% of a matrix selected from the group formed of alumina, silica, magnesia, natural clays, mixtures of said compounds and alumina-boron oxide combinations, (c) 0.01–15% of at least one group VIII metal, and (d) 0.01–1% of at least one group IV B metal (Ti, Zr, Hf).

The catalyst is preferably prepared by introducing the group IV B metal into the matrix, admixing the obtained product with mordenite and then introducing the group VIII metal.

The catalyst is used for hydroisomerizing n-paraffins having 4 to 7 carbon atoms with a good conversion rate and a good selectivity, thus obtaining a mixture comprising a high proportion of isoparaffins.

7 Claims, No Drawings

NORMAL PARAFFIN ISOMERIZATION CATALYST COMPRISING A MORDENITE AND TITANIUM

The present invention concerns a catalyst comprising a particular mordenite whose characteristics ara given hereinafter, at least one metal from group IV B of the periodic classification of elements (Handbook of Chemistry and Physics 6th issue 1980–81) which consists of titanium, at least one group VIII metal and optionally a matrix or binder as hereinafter defined.

The present invention also concerns processes for manufacturing said catalyst and the use thereof for hydrotreating hydrocarbon charges, more particularly for hydroisomerizing cuts containing a high proportion of normal paraffins having 4,5,6 or 7 carbon atoms per molecule.

BACKGROUND OF THE INVENTION

Catalysts comprising at least one group VIII metal, usually platinum, deposited on a carrier, have been used since for a long time for hydroisomerizing n-paraffins, in particular the catalysts comprising as a carrier a halogenated alumina, such for example as those disclosed in U.S. Pat. Nos. 4,116,870 and 4,152,246. Various zeolite carriers have also been used and the applicant has recently disclosed a mordenite of particular characteristics in the European patent application 196,965.

Irrespective of the catalyst type, the isomerization is usually accompanied with a more or less substantial cracking reaction, depending on the catalysts and the operating conditions.

For several years research has been conducted in order to minimize this secondary cracking reaction. Thus, it is advisable for this isomerization reaction to use the catalyst which, in the conditions previously selected for the reaction, will provide for the best isomerization selectivity and the lowest possible cracking selectivity.

SUMMARY OF THE INVENTION

It has been discovered, this being the object of the present invention, that it is possible to substantially improve the performance of the n-paraffin isomerization catalyst, as disclosed in the European patent application 196,965 to the applicant, by incorporating therewith a relatively small amount of titanium. Titanium incorporation with the n-paraffins isomerization catalyst disclosed in EPA 196 965 surprisingly confers on it an increased isomerization selectivity resulting, at isoconversion, in a decrease of the cracking selectivity.

The catalyst that is the object of the invention contains by weight:

(a) 10–99.98 %, preferably 20–90 %, more advantageously 40–85 % of a mordenite of particular characteristics, (b) 0–89.98 %, preferably 5–70 %, more advantageously 10–55 % of a matrix or binder selected from the group formed of alumina, silica, magnesia, natural clays, mixtures of these compounds and alumina-boron oxide combinations, (c) 0.01–15 %, preferably 0.05–10 % of at least one group VIII metal, the preferred metals being platinum, palladium and nickel, the metal content being advantageously of 0.05–1 %, more preferably 0.01–0.6 % for palladium and platinum, advantageously of 0.1–10 % and more preferably of 0.2–5 % for nickel, and (d) 0.01–1 %, preferably 0.02–0.8 % and more advantageously from 0.03 to 0.5 % of titanium.

The mordenite used in the catalyst according to the invention is a mordenite of particular characteristics, prepared from a small-pore mordenite, in such conditions that the resultant mordenite keeps, in major part, its initial morphology (needle shape).

The small-pore mordenite from which is prepared the mordenite used in the catalyst according to the invention generally has a sodium content of about 4 to 6.5 % (by weight) in proportion to the dry mordenite weight; its usual Si/Al atomic ratio is about from 4.5:1 to 6.5:1 and its mesh volume is about from 2.77 to 2.80 cubic nanometers. This initial mordenite only adsorbs molecules of a kinetic diameter of about 4.4 Angstroms.

After treatments, the obtained mordenite is characterized by various specifications whose methods of determination are specified hereinafter:Si/Al atomic ratio of about 5:1 to 100:1, preferably of about 5:1 to 50:1 and advantageously of 5:1 to 30:1, sodium content lower than 0.2% by weight, preferably lower than o.1 % by weight, in proportion to the dry mordenite weight, mesh volume V, of elementary mesh, from 2.73 to 2.78 cubic nanometers (nm3), preferably from 2.74 to 2.77 $nm^3$, benzene adsorption capacity higher than about 5 % and preferably than about 8 % by weight, in proportion to the dry mordenite weight, a particular morphology, in major part as needles. The needles have usually a length from 2 to 20 microns, more particularly 3 to 10 microns, preferably an average length of 5 microns. Their hexagonal faces usually have a length of 0.5 to 4 microns, particularly of 0.5 to 3 microns and a "height" from 0.1 to 2 microns, more particularly 0.2 to 1 micron; preferably the major part (i.e at least 50%) of the hexagonal faces have a length of about 1 micron and a "height" of about 0.3 micron.

The different zeolite characteristics are measured by the following methods:

the total Si/Al atomic ratios are determined by X-ray fluorescence analysis, the sodium contents by atomic absorption, the mesh volume and the crystallinity are determined by X-ray diffraction, the sample being prepared similarly as by the operating mode of Standard ASTM D 3942 80 set up for faujasite, the benzene adsorption capacity of mordenite is determined by gravimetry. The sample is previously desorbed at 300° C. under $10^{-4}$ Torr (1 Torr=133.32 Pa).

The adsorption is then conducted at 30° C. for 4 hours under a benzene pressure P of 28 Torr, corresponding to a P/Ps ratio of 0.25, Ps being the saturating vapor pressure at the temperature of the experiment. The adsorbed volumes are calculated from the density of the adsorbate in the liquid form at the adsorption temperature : d=0.868.

For the purpose of the present invention, mordenite formed in major part of needles is defined as a mordenite containing at least 50 %, preferably at least 75 % and more preferably at least 85 % by weight of needles.

Various methods can be used for obtaining a mordenite having the characteristics and the particular needle morphology as hereabove defined, from a so-called small-pore mordenite.

According to a preferred method, the so-called small-pore mordenite is subjected to the following treatments : the sodium cations are exchanged with ammonium cations by dipping the mordenite into a solution of ionizable ammonium salt of molarity usually higher than 0.5, at a temperature usually of about 20 to 150° C. This exchange may be repeated several times. The product obtained after these cation exchanges may be washed and then subjected to a thermal treatment in the presence of steam, optionally by the self steaming technique (roasting in confined atmosphere). A temperature usually of about 300–800° C., preferably of about 400–700° C., is generally maintained for more than 10 minutes and preferably more than 20 minutes. This thermal treatment usually lasts less than 10 hours and satisfactorily from 30 minutes to 6 hours. The roasting atmosphere contains at least 1 %, preferably at least 5 % of steam. For self-steaming the atmosphere consists essentially of water and ammonia. The obtained product may be subjected to acid treatment for extracting aluminum from the solid. This treatment may be performed by dipping the product into a strong inorganic or organic acid of normality from about 0.1 to 12 N, at a temperature of about 20–150° C., preferably of about 80–150° C., advantageously for more than 10 minutes and usually for about 15 minutes to 10 hours.

After this acid treatment, the product may be washed, for example by means of a diluted acid solution, then washed with water, then optionally admixed to any adequate matrix, selected from the group of the above-mentioned matrices. The use of alumina or of an alumina mixture with one of the above-mentioned compounds containing a major proportion of alumina is preferred.

The obtained product is then shaped and charged for example with platinum and/or palladium and/or nickel. Group VIII metal may be introduced before, after or together with group IV B metal.

When the catalyst comprises a matrix, it is usually preferred to introduce a major part (i.e at least 50 %, preferably at least 75 % and more usually at least 95 % by weight) of the group IV B metal onto the matrix, the group VIII metal being then introduced by any method known in the art, either onto the matrix or onto mordenite. Usually the group VIII metal is preferably introduced, in major part, onto mordenite.

Group IV B metal (titanium) is advantageously introduced onto the matrix, either by mechanical mixing or during the preparation of the matrix. It may also be deposited onto the matrix by any impregnation method known in the art, for example by using aqueous solutions of inorganic or organic metal salts or soluble organic complexes of said metals.

For example, aqueous solutions of titanium tetrachloride ($TiCl_4$), of titanium trichloride ($TiCl_3$) or still of titanium oxalate ($Ti_2(C_2O_4)_3$, 10 $H_2O$) can be used. Titanium may also be introduced as titanium oxide during the mordenite or mordenitematrix mixture shaping step. Titanium is preferably introduced as titanium oxide by mechanical mixing with alumina. Group VIII metal is introduced onto the carrier (mordenite or mordenitematrix mixture) by any known method of the art. When the catalyst comprises a matrix, said metal may be introduced either before or after admixing mordenite with the matrix.

Group VIII metal may thus be introduced for example by means of a solution of organic complex of said metal. When platinum is concerned for example, a solution of a tetrammine platinum salt will be used; when deposited onto a mordenite-matrix mixture, platinum deposits in major part onto mordenite by cation exchange. A solution of inorganic compound of group VIII metal may also be used, for example. For platinum, a solution of hexachloroplatinic acid will be used, for example; when a mordenite-matrix mixture is concerned, platinum then deposits in major part onto the matrix by anion exchange. Group VIII metal may be deposited by means of a solution of organic complex of said metal, either onto the mordenite powder or onto an already shaped product, with or without ammonium competitor cation. This metal may also be deposited onto extrudates or onto powder by the so-called dry impregnation technique. A preferred method for manufacturing the catalyst according to the invention comprises the following steps of:

(a) introducing at least one group IV B metal (titanium) onto the matrix, preferably by mechanical mixing of titanium oxide with the matrix, (b) admixing the resultant product from step (a) with mordenite, (c) introducing at least one group VIII metal onto the resultant product from step (b), preferably after shaping, drying and roasting of said product, and (d) drying and roasting at a temperature of about 300–600° C. the resultant product from step (c).

The use of the catalysts according to the invention, preferably prepared by the above-described preferred method, gives an increased hydroisomerizing activity and selectivity for cuts containing a high proportion of normal paraffins having 4 to 7 carbon atoms per molecule, as compared with hydroisomerization catalysts of the prior art.

The catalysts according to the invention, preferably prepared by the above-mentioned preferred method, may be advantageously used for isomerizing n-paraffins having 4, 5, 6 or 7 carbon atoms per molecule, in the conditions described hereinafter.

According to the invention, the charge, containing a high proportion of light paraffins having 5 or 6 carbon atoms, and hydrogen, is contacted with a catalyst of the above-described type, under isomerization conditions, said catalyst being used as fixed bed, fluidized bed or in batch (i.e in a discontinuous process).

The process is usually performed at a temperature of about 200–300° C., preferably about 230–280° C., under a hydrogen partial pressure in the range from atmospheric pressure (0.1 MPa) to 70 bars (7 MPa) and preferably from 0.5 MPa to 5 MPa. The space velocity is usually from about 0.5 to about 10, preferably from about 1 to 5 liters of liquid hydrocarbons per liter of catalyst and per hour. The hydrogen/hydrocarbon charge molar ratio may vary within a wide range, usually from about 0.5 : 1 to about 10 : 1, preferably from about 1 : 1 to about 5 : 1.

The isomerization being a balanced reaction, the isomerizate still contains a substantial amount of unconverted n-paraffins. These paraffins may be separated from the isomers for example by distillation or by fractionation over molecular sieves and recycled to the isomerization unit.

EXAMPLES

The following examples are given to illustrate the invention and must not be considered as limiting the scope thereof.

The performance is expressed in term of n-hexane conversion rate, of isomerization selectivity and of cracking selectivity, which are defined as follows:

Conversion =

$$\frac{\text{n-hexane input weight} - \text{n-hexane output weight}}{\text{n-hexane input weight}} \cdot 100$$

Isomerisation selectivity = $\frac{\Sigma(\text{weight of isomers}) \cdot 100}{\Sigma(\text{weight of reaction products})}$ Cracking selectivity = 100 − isomerization selectivity Example 1:

Preparation of catalyst A according to the invention

The raw material is a so-called small-pore mordenite manufactured under reference Alite 150 by Socieaue Chimique de la Grande Paroisse. Its chemical formula in anhydrous state is: $Na\ AlO_2\ (SiO_2)_{5.5}$, and its benzene adsorption capacity is 1 % by weight in proportion to the dry solid weight (mesh volume : 2.79 $nm^3$; sodium content: 5.3 % by weight; kinetic diameter of adsorbed molecules : 3.8 Angstroms); 50 g of said powder are dipped into a 2M ammonium nitrate solution and the suspension is brought to 95° C. for two hours.

The ammonium nitrate solution is used in a volume equal to 4 times the weight of dry mordenite (V/P=4). This cation exchange operation is repeated 3 times. After the third exchange, the product is washed with water at 20° C. for 20 minutes with a V/P ratio equal to 4. The sodium content, expressed in percent by weight of the dry weight, decreases from 5.3 to 0.1 %. The product is then filtered and roasted in confined atmosphere (self steaming) at 600° C. for 2 hours.

The product is then subjected to acid etching by 1.3 N nitric acid, at reflux of the product in the nitric acid aqueous solution for 2 hours with a V/P ratio equal to 8. The resultant product is then filtered, washed with 0.1 N nitric acid and then with water.

The Si/Al atomic ratio of said mordenite is 12, its mesh volume 2.750 $nm^3$, its sodium content 300 ppm and its benzene adsorption capacity 9.6 % by weight in proportion to the dry solid weight. This mordenite is shaped as needles having an average length of 5 microns and hexagonal faces of about 1 micron length and 0.3 micron height.

This mordenite is then mixed with an aluminum matrix (25 % by weight) containing 4,000 ppm by weight of titanium oxide. The aluminum matrix was obtained by incorporating titanium oxide with an alumina gel by mechanical mixing. The mordenite-matrix mixture is then forced through a drawing-plate. The extrudates of 1.2 mm are then dried and roasted.

0.4 % platinum is then deposited onto this carrier by cation exchange from platinum tetrammine chloride $Pt(NH^3)_4Cl_2$ with ammonium nitrate as competitor ion. The Si/Al atomic ratio is 12 and the mesh volume 2.750 $nm^3$ The extrudates are then dried and roasted at 500° C.

The final catalyst contains by weight: 24.84 % of alumina, 74.69 % of mordenite, 0.4 % of platinum and 0.06 % of titanium.

The obtained catalyst is charged into a fixed bed catalytic unit and reduced under hydrogen at 450° C. It is then tested with a charge of normal hexane in the following conditions: temperature: 250° C., pressure: 30 bars (3 MPa), n-hexane weight per mordenite weight unit and per hour: 2, hydrogen to normal hexane molar ratio : 2. The performance indicated in table 1 is obtained after 30 hours of run of the catalyst.

Example 2 :

Catalyst B, not conforming with the invention.

Catalyst B differs from catalyst A of example 1 in that mordenite is shaped with an aluminum binder completely free of titanium oxide. The thermal treatments and platinum deposition are performed as precedingly. Catalyst B contains by weight : 24.9 % alumina, 74.69 % mordenite and 0.4 % platinum. Catalyst B is tested in the same conditions as catalyst A. Its performances after 30 hours of run are indicated in table 1.

Example 3 :

Catalyst C, not conforming with the invention.

Catalyst C differs from catalyst A of example 1 by the use of a wide-pore mordenite, as powder manufactured under reference Zeolon 100 Na by NORTON Company.

50 g of said powder are brought to reflux for 2 hours in ammonium nitrate solution. This exchange is repeated 3 times. After the last exchange, the product is washed with water for 20 mn at 20° C., filtered and roasted in confined atmosphere (self steaming) at 600° C. for 2 hours. The thermal treatment is followed by acid etching with 1.3 N nitric acid. The solid is brought to reflux in a nitric acid aqueous solution at 100° C. for 2 hours, then washed with water.

The Si/Al atomic ratio of the obtained mordenite is 12, its mesh volume 2.752 $nm^3$, and its sodium content 95 ppm. Its benzene adsorption capacity is 9.7 % by weight in proportion to the dry solid weight. This product, in contrast with the mordenites used in the present invention, has not a needle shape morphology. The obtained product is then shaped by mixing with a previously peptized alumina gel.

The aluminum matrix was obtained by incorporating titanium oxide with an alumina gel by mechanical mixing. This aluminum matrix contains 4000 ppm by weight of titanium oxide.

The mordenite-matrix mixture containing 25 % by weight of matrix is forced through a drawing plate. The obtained extrudates, of 1.2 mm diameter, are then dried and roasted. 0.4 % platinum is then deposited thereon by the technique described in example 1.

The final catalyst contains by weight : 24.84 % aluminum, 74.69 % mordenite, 0.4 % platinum and 0.06 % titanium. The indicated performances in isocondition reported in table 1 are more than 20 points lower than those obtained with catalyst A according to the invention.

Example 4 :

Catalyst D, not conforming with the invention.

Catalyst D differs from catalyst A of example 1 in that mordenite is shaped with an aluminum binder containing 20 % b weight of titanium oxide. The final catalyst contains by weight : 21.9 % alumina, 74.69 % mordenite, 0.4 % platinum and 3 % titanium. Its performances after 30 hours of run are reported in table 1.

Example 5 :

Catalyst E, not conforming with the invention.

Catalyst E differs from the catalysts of examples 1 to 4 in that the carrier is a chlorinated alumina instead of a mordenite. Here, the catalyst is prepared by adding to 100 g of alumina: 100 cc of a solution containing 1.9 g of concentrated HCl (d=1.19), 20 g of an aqueous solution of hexachloroplatinic acid containing 2 % by weight of platinum and 10 g of an aqueous solution containing 1 % by weight of titanium as titanium tetrachloride. After 2 hours of contact, the catalyst is dried and roasted up to 500° C. The final catalyst contains by weight : 98.46 % alumina, 0.098 % titanium, 0.4 % platinum and 1.04 % chlorine. After reduction in situ, it is tested in the same conditions as the preceding catalysts. Its performances, after 30 hours of run, are reported in table 1.

TABLE I

| CATALYST | CONVERSION RATE % | ISOMERIZA- TION SELEC- TIVITY % | CRACKING SELEC- TIVITY % |
|---|---|---|---|
| A (conforming to the invention) | 81 | 99.0 | 1.0 |
| B | 79.5 | 98.6 | 1.4 |
| C | 57.0 | 96.7 | 3.3 |
| D | 42.3 | 98 | 2 |
| E | 88.7 | 65 | 35 |

What is claimed as the invention is:

1. A catalyst consisting of, by weight:
   (a) 10-99.98 % of a mordenite adsorbing molecules of a kinetic diameter higher than about 6.6 Angstroms, having a Si/Al atomic ratio from about 5 : 1 to 100: 1, a sodium content lower than 0.2 % by weight, in proportion to the total weight of dry mordenite, a mesh volume V of elementary mesh from 2.73 to 2.78 cubic nanometers, a benzene adsorption capacity higher than 5 % by weight in proportion to the dry mordenite weight, said mordenite being in major part shaped as needles,
   (b) 0-89.98 % of a matrix selected from the group formed of alumina, silica, magnesia, natural clays, mixtures of these compounds and alumina-boron oxide combinations,
   (c) 0.01-15 % of at least one group VIII metal, and
   (d) 0.01-1 % of titanium.

2. A catalyst according to claim 1, containing:
   (a) 20-90 % by weight of mordenite,
   (b) 5-70 % by weight of matrix,
   (c) 0.05-10 % by weight of at least one group VIII metal, and
   (d) 0.02-0.8 % by weight of titanium.

3. A catalyst according to claim 1, containing:
   (a) 40-85 % by weight of mordenite,
   (b) 10-55 % by weight of matrix,
   (c) 0.05-10 % by weight of at least one group VIII metal, and
   (d) 0.03-0.5 % by weight of titanium.

4. A catalyst according to claim 1, wherein the group VIII metal is selected from the group formed of platinum, palladium and nickel.

5. A catalyst according to claim 1, wherein the group VIII metal is platinum or palladium, the platinum or palladium content being from 0.05 to 1 % by weight.

6. A catalyst according to claim 1, wherein the matrix is alumina.

7. A catalyst according to claim 1 wherein the mordenite has a Si/Al atomic ratio of about 5:1 to about 50:1, a sodium content lower than 0.1 % by weight, in proportion to the total dry mordenite weight, a mesh volume V of elementary mesh from 2.74 to 2.77 cubic nanometers, a benzene adsorption capacity higher than about 8 % by weight in proportion to the dry mordenite weight, said mordenite being in major part shaped as needles of 2-20 microns length having hexagonal faces of 0.5 to 4 microns length and 0.1 to 2 microns height.

* * * * *